(12) United States Patent
Goossens

(10) Patent No.: US 11,007,359 B2
(45) Date of Patent: May 18, 2021

(54) CONNECTOR FOR CATHETER

(71) Applicant: Canadian Hospital Specialties Limited, Oakville (CA)

(72) Inventor: David George Goossens, Sarnia (CA)

(73) Assignee: Canadian Hospital Specialties Limited

( * ) Notice: Subject to any disclaimer, the term of this patent is extended or adjusted under 35 U.S.C. 154(b) by 284 days.

(21) Appl. No.: 15/897,372

(22) Filed: Feb. 15, 2018

(65) Prior Publication Data
US 2018/0229020 A1    Aug. 16, 2018

Related U.S. Application Data

(60) Provisional application No. 62/459,925, filed on Feb. 16, 2017.

(51) Int. Cl.
*A61M 39/12* (2006.01)
*A61M 1/00* (2006.01)
*A61M 27/00* (2006.01)
*A61M 39/24* (2006.01)

(52) U.S. Cl.
CPC ............ *A61M 39/12* (2013.01); *A61M 1/008* (2013.01); *A61M 1/0039* (2013.01); *A61M 1/0086* (2014.02); *A61M 27/00* (2013.01); *A61M 39/24* (2013.01); *A61M 2210/101* (2013.01)

(58) Field of Classification Search
CPC .. A61M 39/12; A61M 1/0039; A61M 1/0086; A61M 39/0693; A61M 39/24; A61M 2039/2406; A61M 2039/2413; A61M 2039/242; A61M 2039/2426; A61M 2039/2433; A61M 2039/244; A61M 2039/2446; A61M 2039/2453; A61M 2039/246; A61M 2039/2466; A61M 2039/0633; A61M 2039/064; A61M 2039/0646; A61M 2039/0653; A61M 2039/066; A61M 2039/0666
USPC ........................................................ 604/540
See application file for complete search history.

(56) References Cited

U.S. PATENT DOCUMENTS

| 4,874,377 | A | * | 10/1989 | Newgard | A61M 39/045 |
| | | | | | 604/167.02 |
| 5,176,415 | A | * | 1/1993 | Choksi | A61M 39/10 |
| | | | | | 128/202.27 |
| 5,484,401 | A | * | 1/1996 | Rodriguez | A61M 1/008 |
| | | | | | 604/28 |
| 2001/0021829 | A1 | * | 9/2001 | Hiejima | A61M 39/24 |
| | | | | | 604/247 |
| 2003/0070273 | A1 | * | 4/2003 | Kust | A61M 39/26 |
| | | | | | 29/426.1 |
| 2007/0078442 | A1 | * | 4/2007 | Mayse | A61M 39/10 |
| | | | | | 604/533 |

(Continued)

*Primary Examiner* — Adam Marcetich
(74) *Attorney, Agent, or Firm* — Harness, Dickey & Pierce, P.L.C.

(57) ABSTRACT

A connector for use with a pleural catheter that connects securely a drainage tube to a valve of the plural catheter. A system including a fluid receptacle having a negative fluid pressure, a plural catheter having an end designed for implantation into a pleural space of a subject, and an opposite second end having a valve feature, a drainage tube having an end connected to the fluid receptacle and another end having a connector that securely connects the drainage tube to the valve feature of the catheter.

2 Claims, 4 Drawing Sheets

(56) References Cited

U.S. PATENT DOCUMENTS

| | | | |
|---|---|---|---|
| 2009/0177170 A1* | 7/2009 | Kitani | A61M 39/26 604/256 |
| 2009/0256355 A1* | 10/2009 | Wicks | F16L 37/56 285/319 |
| 2009/0292253 A1* | 11/2009 | Raulerson | A61M 39/0693 604/167.04 |
| 2011/0048540 A1* | 3/2011 | Stroup | A61M 39/10 137/1 |
| 2011/0049866 A1* | 3/2011 | Trombley, III | A61M 5/007 285/20 |
| 2015/0025476 A1* | 1/2015 | Downing | A61J 15/0092 604/246 |
| 2015/0238750 A1* | 8/2015 | Williams | A61M 39/26 604/256 |
| 2017/0202741 A1* | 7/2017 | Py | A61M 39/10 |

* cited by examiner

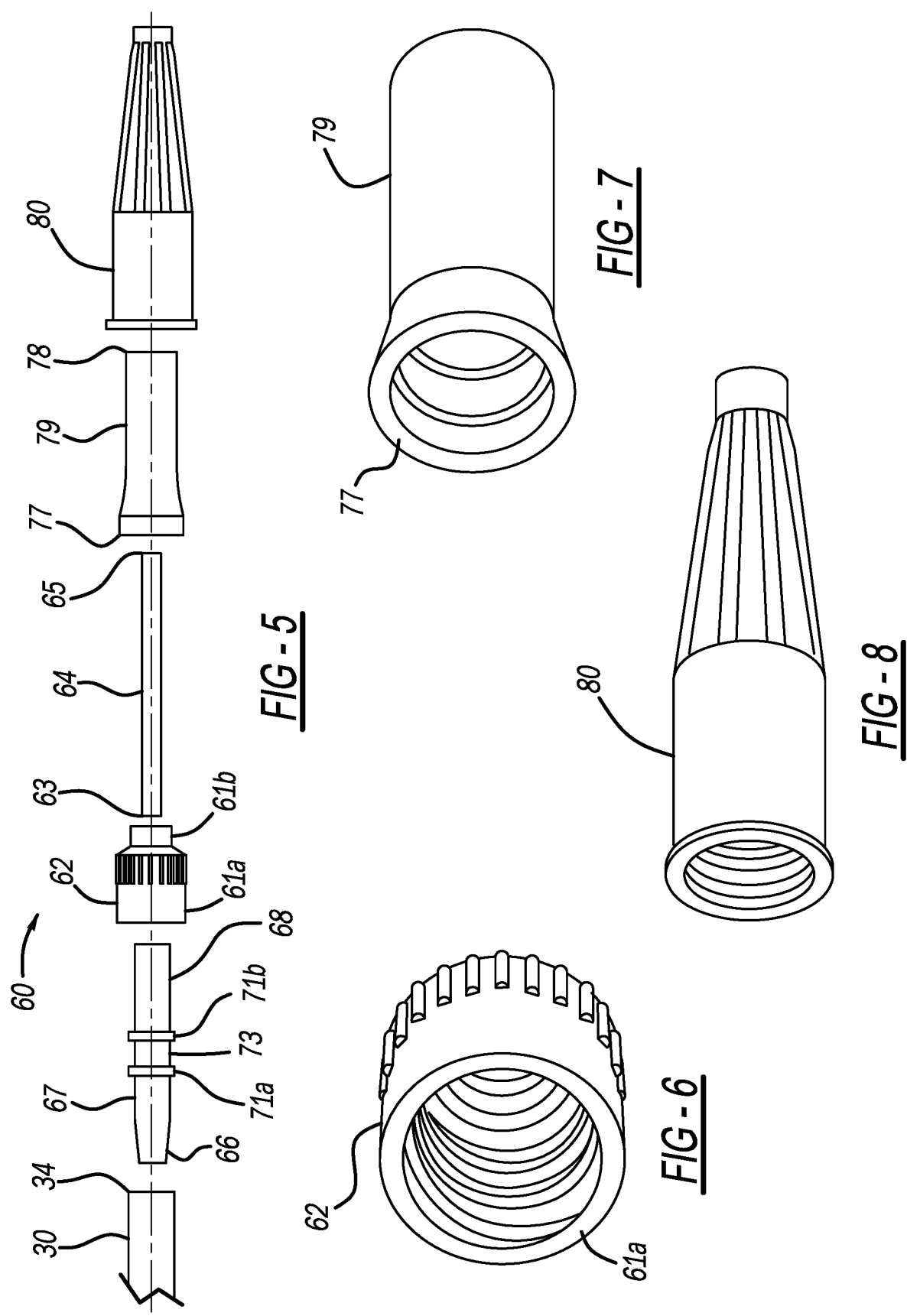

CONNECTOR FOR CATHETER

CROSS REFERENCE TO RELATED APPLICATIONS

This application claims priority from U.S. Provisional Ser. No. 62/459,925, filed Feb. 16, 2017, the content of which is hereby incorporated by reference into the present application.

FIELD OF THE INVENTION

The present invention relates to the field of apparatuses for removing pleural effusion fluids and, in particular, to apparatuses for connecting to a catheter for implantation into the pleural space.

BACKGROUND OF THE INVENTION

Pleural effusion refers to the effusion of fluid into the pleural space. The pleural space normally contains approximately 5 to 20 ml of fluid. A disruption in the balance between the movement of fluid into the pleural space and the movement of fluid out of the pleural space may produce excessive fluid accumulation in the pleural space. Such disruptions may include, for example, (1) increased capillary permeability resulting from inflammatory processes such as pneumonia, (2) increased hydrostatic pressure as in congestive heart failure, (3) increased negative intrapleural pressure as seen in atelectasis, (4) decreased oncotic pressure as occurs in the nephrotic syndrome with hypoalbuminemia, and (5) increased oncotic pressure of pleural fluid as occurs in the inflammation of pleural tumor growth or infection. Pleural effusion is particularly common in patients with disseminated breast cancer, lung cancer or lymphatic cancer and patients with congestive heart failure, but also occurs in patients with nearly all other forms of malignancy.

The clinical manifestations of pleural effusion include dyspnea, cough and chest pain which diminish the patient's quality of life. Although pleural effusion typically occurs toward the end of terminal malignancies such as breast cancer, it occurs earlier in other diseases. Therefore relieving the clinical manifestations of pleural effusion is of a real and extended advantage to the patient. For example, non-breast cancer patients with pleural effusion have been known to survive for years. See "Pleural Effusion in Cancer Patients", Izbicki, et al., Cancer October 1975, p. 1511.

There are a number of treatments for pleural effusion. If the patient is asymptomatic and the effusion is known to be malignant or paramalignant, treatment may not be required. Such patients may develop progressive pleural effusions that eventually do produce symptoms requiring treatment, but some will reach a stage where the effusions and reabsorption reach an equilibrium that is still asymptomatic and does not necessitate treatment.

One approach to removing fluid from the pleural space is to surgically implant a chest tube. Such tubes are commonly quite rigid and fairly large in diameter and are implanted by making a surgical incision and spreading apart adjacent ribs to fit the tube into place. Such procedures are painful to the patient, both initially when the chest tube is inserted and during the time it remains within the pleural space.

Thoracentesis is a common approach to removing pleural fluid, in which a needled catheter is introduced into the pleural space through an incision in the chest cavity and fluid is positively drawn out through the catheter using a syringe or a vacuum source. The procedure may also include aspiration utilizing a separate syringe. There are a number of difficulties in thoracentesis, including the risk of puncturing a lung with the catheter tip or with the needle used to introduce the catheter, the risk of collapsing a lung by relieving the negative pressure in the pleural space, the possibility of aggravating the pleural effusion by stimulating fluid production in the introduction of the catheter, and the risk of infection. One of the primary difficulties with ordinary thoracentesis procedures is that fluid reaccumulates in the pleural space relatively quickly after the procedure is performed, and so it is necessary to perform the procedure repeatedly—as often as every few days. In fact, some studies found that the fluid re-accumulates in one to three days in most cases and re-accumulates within a month in 97% of the cases studied. See "Diagnosis and Treatment of Malignant Pleural Effusion", F. J. Hausheer, J. W. Yarbro, Seminars in Oncology, March 1985, p. 54; "Malignant Effusion", Anderson, et al., Cancer, April 1974, p. 916. Of course, each time the procedure is repeated the risks identified above are heightened. Moreover, the comfort to the patient resulting from the procedure begins to be offset by the discomfort of the procedure itself.

Methods and devices for removing pleural effusion which do not require repeated invasion of the pleural have been developed, for example see U.S. Pat. No. 5,484,401. The device of U.S. Pat. No. 5,484,401 consists of a catheter connected to an end of a drainage tube which in turn is connected though the other end to a vacuum bottle. The catheter and the drainage tube are connected through a valve that is normally closed but can be opened by the insertion of the drainage tube. According to U.S. Pat. No. 5,484,401 the drainage tube needs to be slighter large in diameter than the hole in the hole in the valve so as to produce a seal. The problem with the device described in U.S. Pat. No. 5,484,401 is that this seal between the catheter and the drainage tube can be easily broken. As such, different locking mechanisms have been developed to prevent disengagement between the catheter and the drainage tube. For example see U.S. Pat. No. 8,337,475 which describes a connector to attach the drainage tube to a catheter. The connector of U.S. Pat. No. 8,337,475, however, requires an actual lock.

SUMMARY OF THE INVENTION

Accordingly a drainage system is disclosed herein that includes a connector between the drainage line and the catheter which provides secured attachment to the catheter having a valve such as that described in U.S. Pat. No. 5,484,401.

In one embodiment, the present application discloses a connector that joins a drainage tube to a valve of a catheter, such as the valve described in U.S. Pat. No. 5,484,401, the connector including:

(a) a hollow elongated member having: (i) a first tapered portion configured for fitting within the drainage tube and frictionally holding the connector to the drainage tube, (ii) a second portion having an outer diameter larger than an inner diameter of the drainage tube, and (iii) a space between the first tapered portion and the second portion;

(b) a hollow cannula generally coaxial with the second portion of the elongated member, the hollow cannula having (i) a first portion that is housed within the second portion of the hollow elongated member and spaced away from inner walls of the second portion of the hollow elongated member, and substantially attached to the second portion of the hollow elongated member, and (ii) a second portion that extends beyond a free end of the hollow elongated member;

(c) a collar made of a relatively rigid construction, the collar being coaxial with the hollow elongated member which passes through a bore of the collar, the collar having (i) a first portion that sits within the space of the hollow elongated member, and (ii) a second portion having an inner diameter that is larger than the outer diameter of the drainage tube; and (d) a hollow, substantially flexible sleeve coaxial with the second end of the hollow elongated member, the sleeve having a first end with an inner diameter that is slightly larger than an outer diameter of the first portion of the collar such that the first end frictionally receives the first portion of the collar, and a second end with an outer diameter that is slightly larger than the outer diameter of the valve, such that when assembled, the second end frictionally receives the valve.

BRIEF DESCRIPTION OF THE DRAWINGS

The following figures illustrate various aspects and preferred and alternative embodiments of the invention.

FIG. 5: Exploded view of the connection system illustrated in FIG. 3.

FIG. 6: Perspective view of a collar of the connection system illustrated in FIG. 3.

FIG. 7: Perspective view of a sleeve of the connection system illustrated in FIG. 3.

FIG. 8: Perspective view of a protective cover of the connection system illustrated in FIG. 3.

DESCRIPTION OF THE INVENTION

Definitions

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. In order to aid in the understanding and preparation of the within invention, the following illustrative, non-limiting, examples are provided.

As used in this document, the terms "proximal" and "distal" in this document is relative to the vacuum source. For example, a catheter may have distal and a proximal end. The proximal end refers to the end of the catheter that is on the side of the vacuum source, while the proximal end of the catheter refers to the end that is on the side of the patient.

REFERENCES

Figure 1:
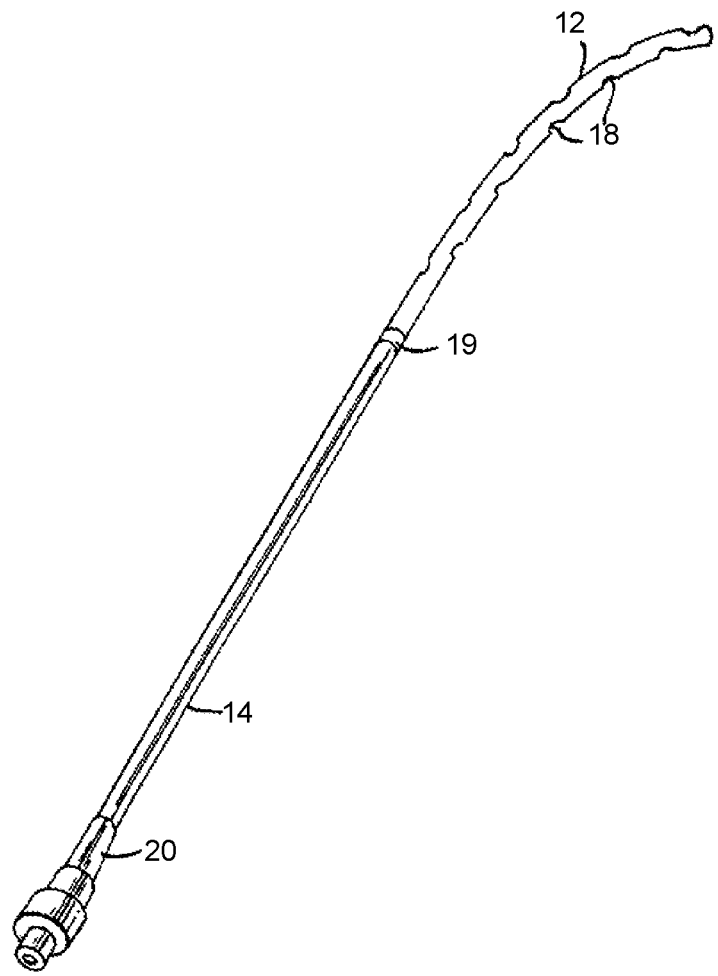
FIG. 1: Prior art catheter described in U.S. Pat. No. 5,484,401.

10: catheter
12: distal end of catheter
14: proximal end of catheter
18: holes
19: Dacron cuff
20: valve feature of catheter
21: elastomeric seal of valve feature 20
22: body of valve feature 20
23: hole in elastomeric seal 21
24: proximal portion of the valve feature 20
25: distal portion of the valve feature 20
26: end of the proximal portion 24
27: Outer wall of the proximal portion 24
28: passageway of valve feature 20
29a: proximal end of the distal portion 25
29b: distal end of the distal portion 25
30: drainage tube
32: first or proximal end of drainage tube
34: second or distal end of drainage tube
50: vacuum source
60: catheter connection system
61a: proximal portion of collar 62
61b: distal portion of collar 62
62: collar
63: first proximal portion of cannula 64
64: cannula
65: second distal portion of cannula 64
66: lower tapered portion of the elongated member 67 (proximal)
67: hollow elongated member
68: upper (distal) portion of hollow elongated member 67
69: end of distal portion 68
72: duckbill valve of valve feature 20
73: space between the spaced apart ridges
77: proximal end of sleeve 79
78: distal end of sleeve 79
79: sleeve A pictorial view of a catheter 10 for use with the present invention is shown in FIG. 1. The catheter 10 has a distal end 12 and a proximal end 14 and may be about twenty-four inches long, the proximal ten inches being fenestrated with a series of holes 18 allowing fluid communication between the exterior of the catheter and the lumen. The catheter is made of a flexible material such as silicone rubber. A few inches distal from the holes 18 may be a Dacron cuff 19.

The catheter is implanted into the pleural space using procedures known in the art. For example, one technique is to make an incision between adjacent ribs of the patient's rib cage in a direction superiorly and posteriorly toward the pleural space. The pleural space is aspirated using a needle and then a J-wire is inserted through the needle and into the pleural space and the needle is removed. A sheath and dilator are threaded over the J-wire and into the pleural space and the J-wire is removed. The dilator is removed from within the sheath. The catheter is then threaded through the sheath and into the pleural space and the sheath is removed.

Figure 2:
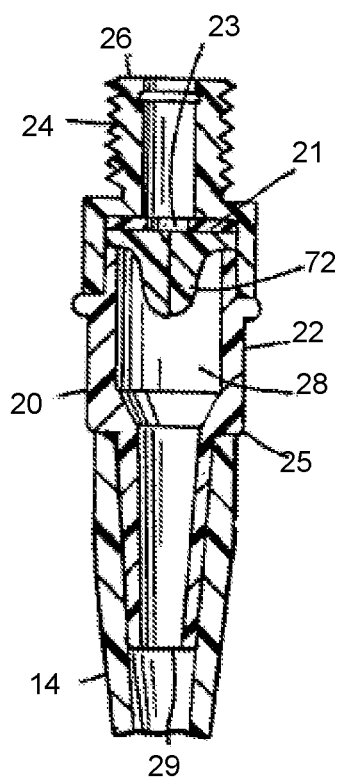
FIG. 2: Cross section view of a self-sealing valve described in U.S. Pat. No. 5,484,401.

The proximal end 14 of the catheter 10 is attached to a valve feature 20. The valve feature 20 is shown in detail in FIG. 2. As shown in FIG. 2, the valve includes a body 22 having a proximal portion 24 and a distal portion 25. The proximal portion has an outer wall. The distal portion 25 has a proximal end and a distal end. The proximal end 26 of the proximal portion 24 and the distal end of the distal portion 25 each have a hole, and the centers of those portions 24 and 25 are hollowed out, thereby forming a passageway 28 through the valve body 22. Positioned within this passageway 28 is a "duckbill" valve 72 which is of the type known in the art consisting of an elastomeric, molded, one-piece dome containing a slit in the center of the domed portion.

The duckbill valve 72 may be opened by inserting an elongated cannula through the passageway 28 from the proximal portion 24 to pry apart the valve. Adjacent to the duckbill valve 72 toward the proximal portion 24 is an elastomeric seal 21. The elastomeric seal 21 is a disk-shaped element having a hole through the center to seal against the outside of the cannula 64. The distal portion 25 is designed for attachment to the proximal end 14 of catheter 10.

The drainage system of the present invention includes, in one embodiment, a catheter 10, a drainage tube 30 for communication of the catheter to a vacuum source or negative pressure source 50.

With reference to FIG. 1, the catheter 10 is an elongated tube that includes a distal end 12 designed for implantation into the pleural space of a subject and an opposite proximal end 14 that is attached to a valve feature 20. The valve feature 20 includes a body 22 having a passageway 24 through the body 22, and self-sealing valve 72 positioned within the passageway 24. The self-sealing valve 72 being closed when the drainage tube 30 is not connected to the valve feature 20, but opens upon connection with the drainage tube 30. The self-sealing valve may be, for example, a "duckbill" one-way type or a disc type one-way valve.

Figure 3:
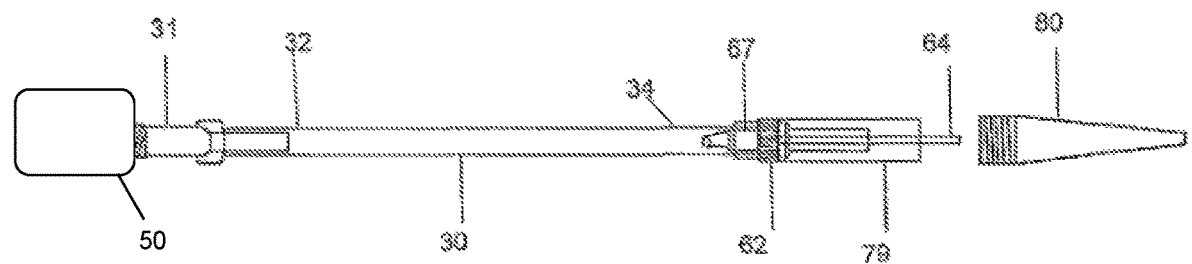
FIG. 3: Cross section view of a drainage tube and the connection system in accordance to one embodiment of the present invention.

With reference to FIG. 3, the drainage tube 30 is an elongated tubing, preferably made of PVC, having a first or proximal end 32 in communication with a vacuum source or negative pressure source 50, and a second distal end 34 having attached a catheter connection system 60 of the present invention for connecting to the valve feature 20 attached to the proximal end 14 of catheter 10. A female Luer lock 31 may be attached to the proximal end 32 of the drainage tube 30 for connection to the vacuum source 50.

Figure 4:
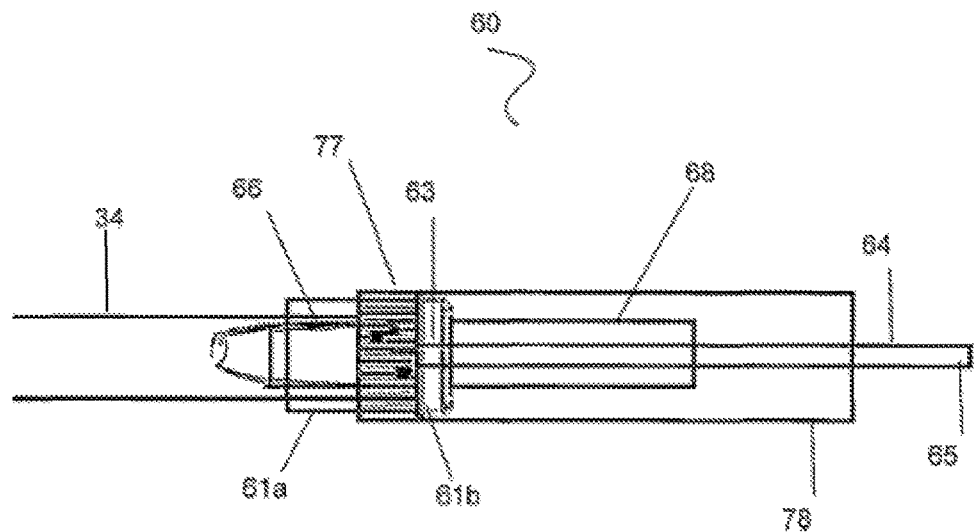
FIG. 4: Expanded view of the connection system illustrated in FIG. 3.

With reference to FIG. 4, the catheter connection system 60 of the present invention includes a retention collar 62, a cannula 64, a hollow elongated member 67, and a sleeve 79.

The cannula 64 may be a tube of thin, somewhat flexible but strong wall construction. The cannula 64 generally defines the longitudinal axis of the present invention and extends to approximately the center of the invention. One end (proximal) of the cannula 64 fixedly attaches to the hollow elongated member 67, which in turn is removable attached to the drainage tube 30.

The hollow elongated member 67 has a lower or first tapered portion 66 and an upper or second portion 68. Between the lower 66 and upper 68 portions two spaced apart ridges 71a and 71b. When assembled, the hollow elongated member extends through the retention collar 62 that sits in the space 73 between the two ridges 71a and 71b. The two ridges 71a and 71b prevent the collar 62 from leaving the space 73. The hollow elongated member 67 may be made of a rigid construction. The tapered portion 66 of the hollow elongated member 67 fits snugly within the drainage tube 30. The lower tapered portion 66 tapers from the ridge 71a and reaches its narrowest diameter at slightly less than the diameter of the drainage tube.

The upper portion 68 has an outer diameter that is similar to that of the distal portion of seal sealing valve, and an inner diameter that is slightly larger than the outer diameter of the cannula 64. The upper portion 68 of the elongated member 67 is generally coaxial with cannula 64, which passes through the upper portion 68 spaced away from the inner walls of the upper portion 68. The cannula 64 has a first proximal portion 63 that is housed within the upper portion 68, and a second distal portion 65 that extends beyond the upper portion 68. The length of the second portion 65 is enough to pass into the passageway of the valve feature and open the one-way valve.

The collar 62 may be made of a rigid construction. The collar 62 is coaxial with the hollow elongated member, which passes through the bore of the collar 62. The collar 62 includes two portions: a proximal portion 61a and a distal portion 61b. The distal portion 61b of the collar sits within space 73. The inner diameter of the distal portion 61b is slightly larger than the diameter of space 73, but smaller than ridges.

The inner diameter of the proximal portion 61a is larger than the outer diameter of the drainage tube 30. The inner walls of the distal portion 61a may include one or more ridges that extend from the inner wall (see FIG. 6).

Sleeve 79 is a hollow flexible tube coaxial with the upper portion 68 of elongated member 67, which in turn is coaxial with the cannula 64. Sleeve 79 includes a proximal end 77 and a distal end 78. The proximal end 77 has an inner diameter that is slightly bigger than the outer diameter of distal portion 61b of collar 62, such as when assembled, the proximal end 77 frictionally receives the distal portion 61b. The inner wall of proximal end 77 of sleeve 79 includes one or more ridges (see FIG. 7). The inner diameter at this ridges is slightly larger than the outer diameter of the upper portion 68 of the elongated member 67, but slightly smaller than the outer diameter of ridge. As such, when assembled, the inner ridges of the proximal end 77 frictionally attach the sleeve 79 to the upper portion 68, while the proximal end 77 frictionally receives and attaches to the distal portion 61b of collar 62.

The outer diameter of the distal end 78 of the sleeve 79 is slightly larger than the outer diameter of the proximal portion 24 of the valve feature 20, but equal or slightly smaller than the outer diameter of the proximal end 29a of the distal portion 25 of valve feature 20.

The length between the proximal end 77 of sleeve 79 and the distal end 78 of sleeve 79 covers the upper (distal) portion 68 of hollow elongated member 67 and a portion of the cannula 64 that extends beyond (i.e. that is not covered by) the distal portion 68 of the elongated member 67.

The connector system 60 of the present invention may also include a protective cover 80 for covering the sleeve 79 and the cannula 64. The protective cover 80 may include a thread (see FIG. 8) designed to engage matching threads in the inner or outer wall of collar 62.

When assembled to the valve feature 20, the cannula 64 enters through the hole in the end 26 of proximal portion 24, through passageway 28, though valve 72, thereby opening valve 72. The cannula 64 continues through passageway 28 until the end 69 of the distal portion of the hollow elongated member 67 abuts with the end 26 of valve feature 20. Simultaneously, the distal end 78 of the sealing sleeve 79 frictionally attaches to the outer wall 27 of the proximal portion 24 and abuts to the proximal end 29a of the distal portion 25, thereby sealing the connection between the connection system 60 of the present invention and the valve feature 20, thereby allowing fluid removal from the pleural cavity into the vacuum source 50. Removal of fluid can be discontinued by simply pulling the connection system 60 from the valve feature 20 thereby disengaging the catheter 10 from the vacuum source 50.

The connector system of the present invention does not require an actual lock, like those of the prior art, but rather is dependent on the vacuum in the vacuum source thereby creating the seal and holding it in place. The outer cuff (sleeve 79), when inserted fully, and vacuum is introduced to the catheter for drainage, creates a "vacuum" seal, that keeps the catheter in place. The hollow elongated member also acts as a safety mechanism, protecting the inner cannula that opens the valve. This keeps the inner cannula in the optimum placement, to keep the valve fully opened. The hollow elongated member also ensures the inner cannula will not be moved on an angle either way, to prevent a change in flow, or damage to the valve or cannula.

Through the embodiments that are illustrated and described, the currently contemplated best mode of making and using the invention is described. Without further elaboration, it is believed that one of ordinary skill in the art can, based on the description presented herein, utilize the present invention to the full extent. All publications cited herein are incorporated by reference.

Although the description above contains many specificities, these should not be construed as limiting the scope of the invention, but as merely providing illustrations of some of the presently embodiments of this invention.

Thus, it should be understood that although the present disclosure has been specifically disclosed by specific embodiments and optional features, modification, improvement and variation of the embodiments therein herein disclosed may be resorted to by those skilled in the art, and that such modifications, improvements and variations are considered to be within the scope of this disclosure. The materials, methods, and examples provided here are representative of particular embodiments, are exemplary, and are not intended as limitations on the scope of the disclosure.

What is claimed is:

1. A connector that joins a drainage tube to a valve of a catheter, the connector including:
   (a) a hollow elongated member having: (i) a first tapered portion configured for fitting within the drainage tube and frictionally holding the connector to the drainage tube, (ii) a second portion having an outer diameter larger than an inner diameter of the drainage tube, and (iii) a space between the first tapered portion and the second portion;
   (b) a hollow cannula generally coaxial with the second portion of the elongated member, the hollow cannula having (i) a first portion that is housed within the second portion of the hollow elongated member and spaced away from inner walls of the second portion of the hollow elongated member, and attached to the second portion of the hollow elongated member, and (ii) a second portion that extends beyond a free end of the hollow elongated member;
   (c) a collar made of a rigid construction, the collar being coaxial with the hollow elongated member which passes through a bore of the collar, the collar having (i) a first portion that sits within the space of the hollow elongated member, and (ii) a second portion having an inner diameter that is larger than the outer diameter of the drainage tube; and
   (d) a hollow, flexible sleeve coaxial with the second end of the hollow elongated member, the sleeve having a first end with an inner diameter that is slightly larger than an outer diameter of the first portion of the collar such that the first end frictionally receives the first portion of the collar, and a second end with an outer diameter that is slightly larger than the outer diameter of the valve, such that when assembled, the second end frictionally receives the valve.

2. A system including:
   (a) a fluid receptacle having a negative fluid pressure,
   (b) a pleural catheter having an end designed for implantation into a pleural space of a subject, and an opposite second end having a valve feature,
   (c) a drainage tube having an end connected to the fluid receptacle and another end having a connector that securely connects the drainage tube to the valve feature of the catheter, wherein the connector comprises:
      (a) a hollow elongated member having: (i) a first tapered portion configured for fitting within the drainage tube and frictionally holding the connector to the drainage tube, (ii) a second portion having an outer diameter larger than an inner diameter of the drainage tube, and (iii) a space between the first tapered portion and the second portion;
      (b) a hollow cannula generally coaxial with the second portion of the elongated member, the hollow cannula having (i) a first portion that is housed within the second portion of the hollow elongated member and spaced away from inner walls of the second portion of the hollow elongated member, and attached to the second portion of the hollow elongated member, and (ii) a second portion that extends beyond a free end of the hollow elongated member;
      (c) a collar made of a rigid construction, the collar being coaxial with the hollow elongated member which passes through a bore of the collar, the collar having (i) a first portion that sits within the space of the hollow elongated member, and (ii) a second portion having an inner diameter that is larger than the outer diameter of the drainage tube; and
      (d) a hollow, flexible sleeve coaxial with the second end of the hollow elongated member, the sleeve having a first end with an inner diameter that is slightly larger than an outer diameter of the first portion of the collar such that the first end frictionally receives the first portion of the collar, and a second end with an outer diameter that is slightly larger than the outer diameter of the valve, such that when assembled, the second end frictionally receives the valve.

\* \* \* \* \*